United States Patent [19]

Monget

[11] Patent Number: 5,336,600
[45] Date of Patent: Aug. 9, 1994

[54] METHOD AND REAGENTS FOR THE DETECTION OF MICROORGANISMS

[75] Inventor: Daniel Monget, Saint Sorlin en Bugey, France

[73] Assignee: Bio Merieux, Charbonnieres Les Bains, France

[21] Appl. No.: 961,625

[22] Filed: Oct. 16, 1992

Related U.S. Application Data

[62] Division of Ser. No. 600,919, Oct. 22, 1990, abandoned.

[30] Foreign Application Priority Data

Oct. 20, 1989 [FR] France ............................ 8914087

[51] Int. Cl.5 .................... C12Q 1/04; C12Q 1/18; G01N 21/76; G01N 1/00
[52] U.S. Cl. ........................................ 435/34; 435/32; 436/63; 436/166; 436/172
[58] Field of Search ............... 435/34, 249, 29, 32; 436/175, 63, 166, 172

[56] References Cited

U.S. PATENT DOCUMENTS

| | | | |
|---|---|---|---|
| 4,830,961 | 5/1989 | Petty | 435/34 |
| 4,983,511 | 1/1991 | Geiger et al. | 435/34 |
| 5,047,321 | 9/1991 | Loken et al. | 435/34 |
| 5,089,395 | 2/1992 | Snyder et al. | 435/34 |

FOREIGN PATENT DOCUMENTS

| | | | |
|---|---|---|---|
| 8403303 | 8/1984 | European Pat. Off. | 435/34 |
| 309848 | 5/1988 | European Pat. Off. | |
| 110958 | 12/1989 | European Pat. Off. | |

OTHER PUBLICATIONS

Nims, R. et al., "Cytosol-Mediated Reduction of Resorufin Fluorescence: Effects on the Ethoxyresorufin O-Deethylase (ETR) Assay," *Biochemical Pharmacology*, vol. 32, No. 1, pp. 175–176, 1983.
Ramsdell, G. et al., "Investigation of Resazurin as an Indicator of the Sanitary Condition of Milk," *Journal of Dairy Science*, vol. XVIII, No. 11, pp. 705–717, 1935.
Johns, D. et al., "Potentiometric Studies with Resazurin and Methylene Blue in Milk," Division of Bacteriology and Dairy Research, Science Service, Department of Agriculture, Ottawa, pp. 295–302, 1939.
Wittrup, K. et al., "A Single-Cell Assay of β-Galactosidase Activity in *Saccharomyces cervisiae*," *Cytometry*, vol. 9, pp. 394–404, 1988.
Enzyme Assays for Food Scientists, pp. 210–212, 1989.
Twigg, R., "Oxidation–Reduction Aspects of Resazurin," *Nature*, vol. 155, pp. 401–402, (1945).
LaBadie, J. et al., "Rapid Counting of Bacterial Flora Isolated from Carcasses of Beef, Pork and Sheep with a Resazurin Test," *Zbl. Bakt. Hyg. 1 Abt. Orig. B.* 179, pp. 217–224 (1984).
Jenneman, G., et al., "Method for Detection of Microorganisms that Produce Gaseous Nitrogen Oxides," *Applied and Environmental Microbiology*, vol. 51, No. 4, pp. 776–780, 1986.
Rao, D., et al., "Rapid Dye Reduction Tests for the Determination of Microbiological Quality of Meat," *Journal of Food Technology*, vol. 21, pp. 151–157, 1986.
Dabbah, R. et al., "Evaluation of the Resazurin Reduction One-Hour Test for Grading Milk Intended for Manufacturing Purposes," pp. 44–48, 1968.
Jenneman, G. et al., "Effect of Nitrate on Biogenic Sulfide Production," *Applied and Environmental Microbiology*, pp. 1205–1211, 1986.

(List continued on next page.)

*Primary Examiner*—Robert J. Warden
*Assistant Examiner*—L. M. Cranford
*Attorney, Agent, or Firm*—Oliff & Berridge

[57] ABSTRACT

A method for the detection of microorganisms brings a sample suspected of containing a microorganism into contact with an aqueous phase reaction medium containing a carbon source and a resorufin marker. The reaction medium is incubated with the sample suspected of containing a microorganism and the fluorescence of the marker during or after incubating is observed. An observed decrease in emitted light indicates the presence of a microorganism.

29 Claims, No Drawings

OTHER PUBLICATIONS

Huddleson, F. et al., "Differentiation of Bacterial Species and Variation within Species by Means of 2,3,5–Triphenyltetrazolium Chloride in Culture Medium," *Science*, vol. 112, pp. 651–652, 1950.

"A Rapid Chemical Test of Total Viability for Suspensions of Tubercle Bacilli", Hm. Rev. Tuberc., vol. 66, pp. 95–98, 1952.

Brown, J. et al., "A Rapid Test for Bacterial Sensitivity to Antibiotics," *American Journal of Clinical Pathology*, vol. 5, No. 1, pp. 10–13, 1961.

Bieringer, G. et al., "Evaluation of a Rapid Dye-Reduction Test for Bacterial Susceptibility to Antibiotics," *The American Journal of Clinical Pathology*, vol. 36, pp. 195–202, 1961.

Hartman, P. et al., "Media and Methods for Isolation and Enumeration of the Enterococci," *Advanced Appl. Microbiol.*, vol. 8, pp. 253–289, 1966.

Pegram, R., "The Microbiological Uses of 2,3,5-Triphenyltetrazolium Chloride," *TTC in Microbiology*, vol. 26, pp. 175–198, 1969.

"A Rapid Method for Determining the Drug Susceptibility of Mycobacterium Tuberculosis," *Resazurin Used as an Oxidation Indicator for Rapid Determination of Drug Susceptibility for MTB*, pp. 111–116, (1957).

DeBaun, R. et al., "On the Mechanism of Enzyme Action. XLIV. Codetermination of Resazurin and Resorufin in Enzymatic Dehydrogenation Experiments," 1950.

Jablonski, J. et al., "Resorufin Inhibits the In Vitro Metabolism and Mutagenesis of Benzo(A)Pyrene," *Biochemical and Biophysical Research Communications*, vol. 136, No. 2, pp. 555–562, 1986.

Kanazawa, Y. et al., "Resazurin Disc Method for Rapid Determination of Drug-Sensitivities of Microorganisms," *The Journal of Antibiotics. Ser. A*, vol. XIX, No. 5, pp. 229–232, 1966.

Roller, S. et al., "Electron-Transfer Coupling in Microbial Fuel Cells: 1. Comparison of Redox-Mediator Reduction Rates and Respiratory Rates of Bacteria," *J. Chem. Tech. Biotechnol*, vol. 34B, pp. 3–12, 1984.

Johns, C. et al., "The Effect of Residual Penicillin in Milk on the Dye Reduction Tests for Quality," *Canadian Journal of Agricultural Science*, vol. 33, pp. 91–97, Ottawa, 1952.

Guilbault, G., "Fluorometric Determination of Dehydrogenase Activity Using Resorufin," *Fluorometric Determination of Dehydrogenase*, pp. 53–56.

Little, L., "Comparative Studies Upon the Methylene Blue and Resazurin Tests," *Journal of Milk Technology*, pp. 274–279.

Proctor, B. et al., "Redox Potential Indicators in Quality Control of Foods," 1939.

Kanazawa, Y. et al., "Niigara Railway Hospital", 1966.

Greene, V. et al., "Influence of Bacterial Interaction on Resazurin Reduction Times," *J. Dairy Science*, vol. 42, pp. 1099–1100.

METHOD AND REAGENTS FOR THE DETECTION OF MICROORGANISMS

This is a division of application No. 07/600,919 filed Oct. 22, 1990, now abandoned.

BACKGROUND OF THE INVENTION

The present invention relates generally to the detection of microorganisms in various media or on various substrates, for various purposes or applications, such as microbial detection or identification.

More specifically, the invention is concerned with reagents comprising an aqueous-phase reaction medium which contains at least one carbon source as well as a luminescent marker, a luminous emission of which is capable of modification as a result of the growth or metabolism of the microorganism to be detected, introduced into the reaction medium.

Microorganism is understood to mean, in particular, microbes, bacteria and yeasts.

"Luminous emission" is understood to mean any luminous radiation emitted under the effect of an external excitation, in particular luminous excitation, in the visible region or otherwise, capable of being modified by the growth of the microorganism in the reaction medium, and of being observed, monitored or measured by all means of optical detection, including simple observation with the naked eye. From this definition, various luminous properties are apparent, such as luminescence, fluorescence and phosphorescence, visible or otherwise to the naked eye, for example.

Description of the Prior Art

For many years, manufacturers and specialists dealing with reagents or methods for the detection of microorganisms have been seeking a design protocol possessing jointly the following essential features:

being universal in nature, that is to say independent of the type or species of microorganisms being tested for being substantially independent of the nature of the medium or substrate in which the microorganisms are being tested for possessing great sensitivity.

None of the methods available to date, including the most recent, enable all these requirements to be satisfied, as shown and detailed below.

A first, and the simplest, method consists in withdrawing a sample, diluting the latter successively, where appropriate, and applying the sample obtained to the surface of a nutrient agar medium. After incubation for 24 to 48 hours, checking of the presence of microorganisms and, where appropriate, their counting are performed by manual or video means. The technique which consists in immersing slides impregnated with a nutrient medium directly in the medium being checked, and monitoring, after incubation, the presence of microorganisms on these slides, constitutes, in fact, a variant of this first method.

Such an approach is of low sensitivity and unreliable, especially when video monitoring means are used. Such a method also requires the nutrient medium to be adapted or selected in accordance with the microorganisms being tested for.

A second method, quite similar to the first, consists in pigmenting or staining the sample withdrawn, or inducing its fluorescence, with any suitable substance such as acridine orange, and then observing the sample so treated directly, for example under a microscope. In essence, such a method possesses drawbacks comparable to those of the first method; in particular, such an approach remains manual and its automation is seen to be difficult.

A third method consists in withdrawing a sample and culturing the latter for a predetermined time, and then observing the culture medium by nephelometry or turbidimetry. In other words, the presence of microorganisms is revealed by the opacity of the culture medium. Such a method is seen to be rather insensitive, and the observed opacity does not result only from the presence of microorganisms, so that this approach is seen to be unusable or incapable of exploitation for complex biological media, for example blood samples.

Various more elaborate methods, with a biochemical basis and employing coloretry or fluorimetry, have been proposed for detecting microorganisms.

A fourth method consists in bringing into contact a sample to be monitored and a reagent comprising a carbohydrate such as glucose, and a pH indicator. Since growth or metabolism of the microorganism generates acids, the latter change the color of the pH indicator. Such an approach proves to be rather insensitive and, in any case, is not universal in nature.

A fifth method consists in bringing into contact a sample to be monitored and an oxidation/reduction chromogenie indicator such as a tetrazolium salt. The biochemical mechanisms of the respiratory chain of the microorganisms present generate reducing substances such as NADH (hydrogenated nicotinamide adenine dinucleotide); this reducing substance leads to reduction of the indicator and hence to its change of color. Such a method is rather insensitive and, in particular, the tetrazolium salts have to be used in large amounts. It will thus be noted that the latter are toxic and precipitate readily.

A sixth method consists in using chromogenic or fluorogenic synthetic enzyme substrates. The presence of certain enzymes linked to the growth of the microorganisms leads to the enzyme substrate being cut in half, and to the chromogenic or fluorogenic portion being liberated, which portion can then be detected.

Such a method is not universal in nature, in the sense that the enzyme substrate must be matched on each occasion to the type of microorganism being tested for; in particular, there is no single enzyme common to all microorganisms. Moreover, for complex biological media such as blood or urine, already containing enzymes, this method does not permit those specific to the microorganisms, for example bacteria or microbes, whose presence is being tested for, to be distinguished.

A seventh method consists in detecting the microorganisms via the metabolite ATP (adenosine triphosphate) in the presence of a luciferin substrate, and by oxidation of the latter in the presence of luciferase, which leads to bioluminescence of the aforementioned substrate. Such a method possesses, in essence, the same drawbacks as those stated for the previous method.

An eighth method involves detection of the carbon dioxide produced by the microorganisms in the presence of one or more carbon sources in the reaction medium; such a technique is, for example, used in hemoculture for detecting a microbial presence. The detection of carbon dioxide may be radiometric, in which case a $^{14}C$-labeled carbon source must be used, or spectrophotometric in the infrared. It is also possible to measure the production of carbon dioxide by monitoring the increase in pressure in a closed system using a manometer or a suitable pressure sensor. Such a method is rather insensitive and, in the case of a radioactive label, it creates various problems of safety and prior administrative consent on the part of the measuring laboratory.

A final method consists in detecting the microorganisms by means of the changes in the electrical parameters of the reaction medium in which the microorganisms are growing; these parameters being, in particular, impedance, conductance or capacitance. On the basis of this method, different biosensors have been developed and marketed, in particular in the agri-foodstuffs field. Such a technique is rather insensitive, in particular with respect to the requirements of diagnosis for medical purposes. And the equipment currently available according to this approach is rather inefficient.

This analysis of the previous approaches regarding detection of microorganisms being concluded, it will be observed in passing that some of these methods involve sampling, that is to say withdrawal of a sample from the medium or from the substrate to be monitored, culturing of this sample and, where appropriate, sampling of the culture medium at regular intervals. Such operations, in general performed manually, appear to be difficult to automate.

SUMMARY OF THE INVENTION

The subject of the present invention is a reagent for the detection of microorganisms, with a luminescent marker, avoiding most of the drawbacks previously observed. More specifically, the subject of the present invention is a reagent and a corresponding detection method simultaneously permitting:

detection of the microorganisms directly on the medium or sample to be monitored, the possibility of automation, in view of the simplicity of the analytical method adopted, universal nature, that is to say substantially independent of the medium in which the microorganisms are being tested for, and of the nature or species of the latter, and good sensitivity, especially detection at relatively low concentrations.

As a result of the experimental discovery described below, a reagent has been found satisfying all the above requirements.

This experimental procedure was as follows:

Through the action of β-glucuronidase of Escherichia coli cultured in a suitable broth, it is possible to cut the substrate 4-methylumbelliferyl-βDglucuronide, to liberate in this way fluorescent 4-methylumbelliferone and hence to detect the aforementioned bacterium.

1st Experiment

By replacing the substrate 4-methylumbelliferyl-β-D-glucuronide by the substrate resorufin β-D-glucuronide to test for E. coli β-glucuronidase in the same broth, it was found that, although the new substrate is hydrolyzed during the bacterial growth in a vial, the pink fluorescence of resorufin is not expressed; at the very most, a pink edging is obtained at the broth/gaseous atmosphere interface, while resorufin is soluble in aqueous media.

2nd Experiment

Free resorufin at a concentration of 20 micromoles/liter is introduced into sterile vials containing the same broth as above. The vials are then inoculated with various bacterial strains of enterobacteria on the basis of $10^6$ bacteria/ml.

At the start, the broth is pink in all the vials (resorufin fluorescence).

After more than 4 hours of incubation at 37° C., the medium in the vials showing growth is decolorized (sometimes with a pink edging at the surface), whereas the control without bacterium remains pink.

CONCLUSION FROM THESE TWO EXPERIMENTS

Bacterial growth in broth in the presence of resorufin brings about the disappearance of the fluorescence of this marker.

Although the nature of the reaction in question cannot be identified with certainty, resorufin is seen to be an excellent indicator of bacterial growth.

On the basis of this discovery, the present invention proposes, in the first place, a reagent for the detection of microorganisms, comprising an aqueous-phase reaction medium containing at least one carbon source and one nitrogen source, as well as a fluorescent marker consisting of resorufin or orcirufin or all anionic forms of these chemical compounds. These two products correspond to the formulae shown below, respectively:

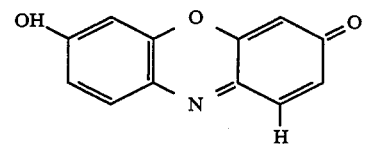

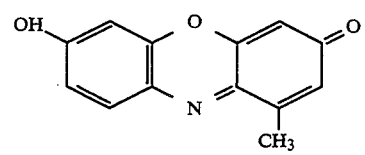

Since the fluorescence of the abovementioned markers has as its origin a substantial electron delocalization between positions 3 and 7, generating a resonance hybrid according to the following formula:

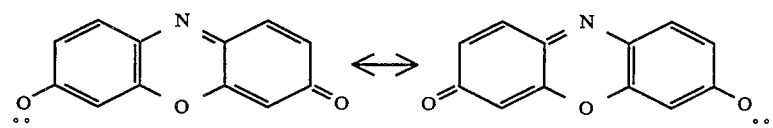

the present invention has been concerned, by way of a marker, with the related chemical structures corresponding to the two general formulae below, and also possessing fluorescence properties which are usable in the context of a reagent according to the invention for the detection of microorganisms.

The chemical compounds in question are, in the first place, those corresponding to the following formula, in neutral or anionic form:

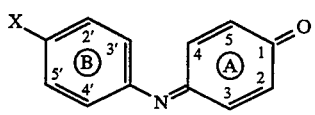

in which:

positions (2'), (4') and (5') are each occupied by a hydrogen atom or a substituent selected from the group comprising fluorine, chlorine, bromine and alkyl, alkoxy, carboxylate, carboxyl, amide and cyano substituents, an oxy group links positions (3') and (4) to one another, positions (2), (3) and (5) are each occupied by a hydrogen atom or a substituent selected from the group comprising fluorine, chlorine, bromine and alkyl, alkoxy, carboxylate, carboxyl, amide and cyano substituents, or positions (2) and (3) belong in common to the ring (A) and to an unsaturated ring, and X is a hydroxyl or amine function.

The chemical compounds in question are, next, those in neutral or anionic form corresponding to the following formula:

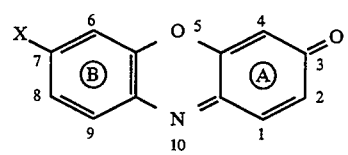

in which positions (6, 8, 9) are each occupied by a hydrogen atom or a substituent selected from the group comprising fluorine, chlorine, bromine and alkyl, alkoxy, carboxyl, amide and cyano substituents, A in which positions (1) and (4) are each occupied by an atom or substituent selected from the group comprising hydrogen, fluorine, chlorine, bromine and alkyl, alkoxy, carboxylate, carboxyl, amide and cyano substituents; or positions (1) and (2) belong in common to the ring (A) and to an unsaturated ring, and X is a hydroxyl or amine function.

Compounds corresponding to the latter general formula, as well as their method of production, are specified in the table below.

| Compound name | X | Substituent 1 | 2 | 4 | 6 | 8 | 9 | PRODUCTION |
| --- | --- | --- | --- | --- | --- | --- | --- | --- |
| Resorufin | OH | H | H | H | H | H | H | Condensation N-chloroquinone monoimine (2) with resorcinol; or reduction, then aerial oxidation of resazurin (3); or heating resorcinol, nitrobenzene and sulfuric acid, neutralization then ethanol extraction |
| Orcirufin | OH | CH$_3$ | H | H | H | H | H | Condensation N-chloroquinone monoimine (2) with orcinol |
| Resorufamine | NH$_2$ | H | H | H | H | H | H | Condensation N,N'-dichloroquinone diimine (1) and resorcinol |
| Orcirufamine | NH$_2$ | CH$_3$ | H | H | H | H | H | Condensation N,N'-dichloroquinone diimine (1) and orcinol |
| Methylorcirufin | OH | CH$_3$ | H | H | H | H | CH$_3$ | Reaction in ether solution of orcinol with fuming nitric acid to obtain dimethylresazurin; reduction, then aerial oxidation of the dimethylresazurin |
| Pentylresorufin | OH | C$_5$H$_{11}$ | H | H | H | H | H | ditto methylorcirufin, from olivetol (5-pentylresorcinol) |
| 2-Chhlororesorufin | OH | H | Cl | H | H | H | H | ditto methylorcirufin, but from 4-chlororesorcinol |
| 6,8-Dichloro-1-methylresorufin | OH | CH$_3$ | H | H | Cl | Cl | H | Condensation Gibb's reagent (4) with orcinol |
| 6,8-Dibromo-1-methylresorufin | OH | CH$_3$ | H | H | Br | Br | H | Condensation Gibb's reagent (4) with orcinol |
| 3-Methoxyresorufin | OH | OCH$_3$ | H | H | H | H | H | ditto methylorcirufin, but from 5-methoxyresorcinol |
| 2-Carboxyresorufin | OH | H | CO$_2$H | H | H | H | H | Condensation N-chloroquinone monoimine (2) with β-resorcinic acid (2,4-dihydrobenzoic acid) |
| Naphthoresorufin | OH | | 1,2-benzo | H | H | H | H | Condensation N-chloroquinone monoimine (2) with naphthoresorcinol |
| 4-Methylresorufin | OH | H | H | CH$_3$ | H | H | H | Condensation |
| 2,4,6,8-Tetrabromo-resorufin | OH | H | Br | Br | Br | Br | H | Direct halogenation of resorufin (or orcirufin) |
| 2,4,6,8-Tetrachloro-resorufin | OH | H | Cl | Cl | Cl | Cl | H | Direct halogenation of resorufin (or orcirufin) |

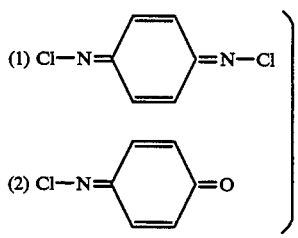

Obtained from p-aminophenol according to Willstatter and Mayer, Ber (1904) 37,1498 et seq.

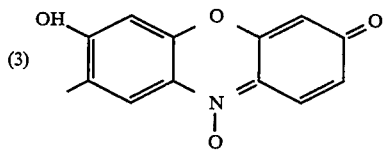

(3)

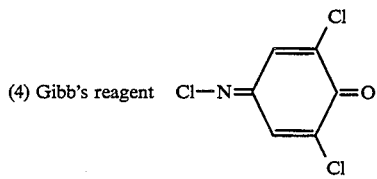

(4) Gibb's reagent

According to the present invention, the following conditions are employed:

the pH of the reaction medium is between 6.0 and 8.0, the indicator or marker is contained in the reaction medium, in the proportion of 0.01 mg/l to 100 mg/l and preferably 1 to 10 mg/l, the nitrogen source in the reaction medium can be of any kind, for example peptone or ammonium sulfate, and the carbon source can be of all types, such as glucose, lactose or the like.

In respect of the reaction medium containing the nitrogen and carbon sources necessary to the reagents, the majority of commercially available broths can be suitable, for example tryptone soybean, brain heart, and the like.

A detection method according to the invention consists in carrying out the following steps:

1) The reagent comprising, as above, the reaction medium and the marker according to the invention, is prepared, distributed in bottles or vials or any other forms of packaging and sterilized by filtration or autoclaving.

2) The reagent is mixed with the sample, medium or substrate to be monitored.

3) The mixture obtained is incubated at between 20° and 65°, for a time between 1 minute and 7 days, for example.

4) The fluorescence of the marker is measured at regular intervals using a fluorimeter, or simply assessed with the naked eye.

The decrease in the fluorescence, or even its complete extinction, reflects the presence of microorganisms in the sample or substrate being monitored.

The present invention is now described and detailed in respect of the experiments performed in relation to resorufin. This marker further provides the following additional important advantages:

this product is not toxic, it possesses great sensitivity, permitting its use at very low concentrations, of the order of 1 to 2 mg/l and above all, in respect of the fluorescence, the wavelengths of maximum excitation and emission lie at 572 nm and 585 nm, respectively; these wavelengths lie beyond those of the radiation absorbed by most of the media or samples analyzed, while remaining within the visible region, thereby enabling the fluorescence specific to resorufin to be observed separately without interference or problems caused by the surrounding medium.

EXAMPLE 1: Preparation of the Reagent

The reaction medium is prepared by mixing the following ingredients:

| | |
|---|---|
| dehydrated Mueller Hinton broth (Difco, ref 0757-01) | 21 g |
| glucose (Merck, ref 8337) | 5 g |
| resorufin (Aldrich, ref 23015-4) | 2 mg |
| distilled water | 1,000 ml |
| pH | 7.3 |

This medium is distributed in screw-capped glass tubes on the basis of 6 milliliters per tube and autoclaved at 121° C. for 15 minutes.

The sterilized tubes are stored in the dark, resorufin being light-sensitive.

This medium will be used in Application Examples 2 to 4 according to the following general method: after the component or various components specific to the application in question have been added, the screw-capped tubes are agitated in an incubator on a Vibratest mixer adjusted to 100 rpm. The fluorescence measurement is performed using an LKB type LS - 5B fluorimeter. The tubes are introduced directly into the cell carrier. The wavelength of excitation is adjusted to 572 nm and that of emission to 585 nm. It should be noted that, in Example 4, the glucose present in the reaction medium may be replaced by other sugars.

EXAMPLE 2: Application to Hemoculture

Sterile fresh human blood is added on the basis of 1 milliliter per tube to 7 glass tubes containing the reagent prepared according to Example 1.

The first tube is used as a control and the other 6 are inoculated with one of the following 6 microbial strains:

| | |
|---|---|
| Ec = | *Escherichia coli* |
| Cf = | *Citrobacter freundii* |
| Pa = | *Pseudomonas aeruginosa* |
| Sa = | *Staphylococcus aureus* |
| Ef = | *Enteroccocus faecalis* |
| Ca = | *Candida albicans* |

The quantity of microorganisms introduced at the beginning into each tube is 100 viable cells per milliliter of medium. This inoculum is checked by counting the colonies formed at the surface of a blood agar after 24 hours' incubation.

The fluorescence measurement is performed after 12 h, 24 h, 36 h and 48 h of incubation at 35° C.

The fluorescence intensity is recorded in the table below. Partial or complete extinction of the fluorescence is evidence of the presence of microbial cells in the initial samples

| Incubat. | Strain | | | | | | |
|---|---|---|---|---|---|---|---|
| | Negative control | Ec | Cf | Ps | Sa | Ef | Ca |
| 12 H | 463 | 11 | 454 | 465 | 447 | 459 | 461 |
| 24 H | 465 | 9 | 10 | 464 | 460 | 126 | 460 |
| 36 H | 458 | 8 | 10 | 58 | 27 | 13 | 461 |
| 48 H | 464 | 9 | 9 | 17 | 13 | 18 | 19 |

For this application, it is preferable to use a broth specific to hemoculture in place of Mueller Hinton broth.

EXAMPLE 3: Antibiogram Application 6 different antibiotics are introduced into tubes prepared as described in Example 1. Each antibiotic is used at the 2 concentrations "c" and "C" shown in the table below. Tubes without antibiotics are used as controls.

Each pair of tubes corresponding to an antibiotic at the 2 concentrations "c" and "C" is inoculated with one of the following 3 microbial strains on the basis of 10 viable cells per milliliter:

| Ec = | *Escherichia coli* | ATCC 25922 |
|---|---|---|
| Pa = | *Pseudomonas aeruginosa* | ATCC 27853 |
| Sa = | *Staphylococcus aureus* | ATCC 25923 |

The fluorescence measurement is performed after 18 hours' incubation at 35° C. The fluorescence intensity is recorded in the table below.

The results are designated by the following symbols:

| S = | sensitive strain = | maximum fluorescence |
|---|---|---|
| R = | resistant strain = | complete extinction of the fluorescence |
| I = | intermediate strain = | partial extinction of the fluorescence |

The antibiogram is checked by the agar dilution technique.

| Antibiotic | Concentration in μg/ml | Ec | Pa | Sa | | | |
|---|---|---|---|---|---|---|---|
| Control | c = 0 | 8 | | 10 | | 9 | |
| | C = 0 | 7 | | 11 | | 11 | |
| Penicillin | c = 0.25 | 9 | R | 10 | R | 455 | S |
| | C = 16 | 8 | | 9 | | 457 | |
| Piperacillin | c = 32 | 460 | S | 463 | S | 459 | S |
| | C = 128 | 465 | | 450 | | 468 | |
| Cefoxitin | c = 8 | 439 | S | 15 | R | 448 | S |
| | C = 32 | 463 | | 9 | | 457 | |
| Renamycin | c = 2 | 15 | I | 13 | R | 438 | S |
| | C = 16 | 458 | | 10 | | 447 | |
| Tetracycline | c = 1 | 451 | S | 15 | R | 443 | S |
| | C = 4 | 465 | | 19 | | 459 | |
| Erythromycin | c = 1 | 8 | R | 11 | R | 445 | S |
| | C = 4 | 10 | | 13 | | 460 | |

Preparation of the antibiogram according to the invention may be carried out in miniaturized cups (microtitration plate).

EXAMPLE 4: Application

The utilization of 7 different sugars by 8 microbial strains for purposes of identification is presented in this example:

| Glucose | (GLU) |
|---|---|
| Maltose | (MAL) |
| Sucrose | (SAC) |
| Lactose | (LAC) |
| Cellobiose | (CEL) |
| Trehalose | (TRE) |
| Melibiose | (MEL) |

The tests are performed in the reagent in glass tubes, prepared as described in Example 1. The glucose contained in this medium is replaced, where appropriate, by the corresponding sugar at the same concentration of 5 g/l.

The array of tubes is inoculated by the following 8 strains:

| Ca = | *Candida albicans* |
|---|---|
| Ct = | *Candida tropicalis* |
| Tg = | *Torulopsis glabrata* |
| Ec = | *Escherichia coli* |
| Kp = | *Klebsiella pneumoniae* |
| Pv = | *Proteus vulgaris* |
| Ah = | *Aeromonas hydrophila* |
| Va = | *Vibrio alginolyticus* |

For each strain, a suspension is prepared in physiological saline and adjusted to point 2 of McFarland's scale. 200 microliters of this suspension are introduced into the 7 tubes containing each of the sugars.

The fluorescence measurement is performed after 18 hours' incubation at 35° C. The fluorescence intensity is recorded in the table below. The results are designated by the following symbols:

| negative reaction ... (−) = | maximum fluorescence |
|---|---|
| positive reaction ... (+) = | extinction of the fluorescence |

The results obtained are checked using micromethods marketed with the tests marketed under the brand name API by the company BIO MERIEUX under the names API 20 E, API 20 C and API 50 CH.

| Strain | Sugar | | | | | | |
|---|---|---|---|---|---|---|---|
| | GLU | MAL | SAC | LAC | CEL | TRE | MEL |
| Ca | 31 | 25 | 37 | 466 | 453 | 19 | 439 |
| | + | + | + | − | − | + | − |
| Ct | 12 | 17 | 21 | 441 | 16 | 20 | 452 |
| | + | + | + | − | + | + | − |
| Tg | 12 | 456 | 447 | 452 | 449 | 16 | 465 |
| | + | − | − | − | − | + | − |
| Ec | 9 | 13 | 459 | 10 | 454 | 10 | 11 |
| | + | + | − | + | − | + | + |
| Kp | 10 | 9 | 9 | 11 | 8 | 10 | 8 |
| | + | + | + | + | + | + | + |
| Pv | 9 | 469 | 10 | 458 | 461 | 437 | 456 |
| | + | − | + | − | − | − | − |
| Ah | 10 | 14 | 11 | 451 | 467 | 12 | 444 |
| | + | − | + | − | − | + | − |
| Va | 11 | 10 | 8 | 469 | 451 | 10 | 449 |
| | + | + | + | − | − | + | − |

The utilization of carbon sources for purposes of identification according to the invention may be carried out in miniaturized cups (microtitration plates, for example).

Accordingly, the reagents according to the invention may be used for the detection of microorganisms in all types of biological samples, such as body fluids (blood, urine, cerebrospinal fluid, and the like), foodstuffs, water, pharmaceutical products, cosmetics, and the like.

In a similar manner to the antibiogram according to Example 3, the invention may be used to prepare an antifungigram, in which case a plurality of reagents according to the invention, differing from one another only by the addition of different antifungal agents, respectively, is used.

I claim:

1. A method for the detection of microorganisms such as microbes, bacteria and yeasts, comprising the steps of:
    bringing at least one sample suspected of containing a microorganism into contact with at least one aqueous phase reaction medium containing at least one carbon source and a marker, said marker emitting light by fluorescence directly without hydrolytic splitting and being a chemical compound corresponding to a member selected from the group consisting of the following formula, and its anionic form:

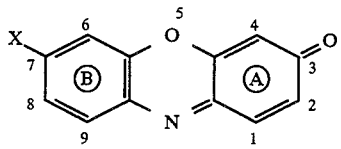

in which:
        positions (4), (6), (8) and (9) are each occupied by one of a hydrogen atom and a substituent selected from the group consisting of fluorine, chlorine, bromine and alkyl, alkoxy, carboxylate, carboxyl, amide and cyano substituents;
        positions (1) and (2) are each occupied by one of a hydrogen atom and a substituent selected from the group consisting of fluorine, chlorine, bromine and alkyl, alkoxy, carboxylate, carboxyl, amide and cyano substituents, or positions (1) and (2) belong in common to the ring (A) and to an unsaturated ring;
        and X is one of a hydroxyl and amine function;
    incubating said at least one reaction medium with said at least one sample suspected of containing a microorganism;
    observing the fluorescence of the marker whereby an observed decrease in the emitted light indicates the presence of a microorganism in said at least one sample.

2. The method according to claim 1, wherein the marker is selected from the group consisting of resorufin, orcirufin, resorufamine, orcirufamine, methylorcirufin, pentylresorufin, 2-chlororesorufin, 6,8-dichloro-1-methylresorufin, 6,8-dibromo-1-methylresorufin, 3-methoxyresorufin, 2-carboxyresorufin, naphthoresorufin, 4,-methylresorufin, 2,4,6,8-tetrabromoresorufin, 2,4,6,8,-tetrachlororesorufin and their anionic forms.

3. The method according to claim 1, wherein the marker is present in an amount of from about 0.01 mg to about 100 mg per liter of reaction medium.

4. The method according to claim 3, wherein the marker is present in an amount of from about 1 mg to about 10 mg per liter of reaction medium.

5. The method according to claim 1, wherein the reaction medium further comprises a nitrogen source.

6. The method according to claim 1, wherein the step of incubating is performed for a time period from about 1 minute to about 7 days.

7. The method according to claim 1, wherein the step of incubating is performed at a temperature of from about 20° C. to about 65° C.

8. The method according to claim 1, wherein said at least one sample suspected of containing a microorganism is a body fluid.

9. The method as claimed in claim 8, wherein the body fluid is selected from the group consisting of blood, urine and cerebrospinal fluid.

10. The method according to claim 1, wherein the sample is a selected from the group consisting of food stuffs, water, pharmaceutical products and cosmetics.

11. The method according to claim 1, wherein aliquots of said sample are brought into contact with a plurality of said aqueous phase reaction media.

12. The method according to claim 11, wherein each said aqueous reaction medium contains a different carbon source.

13. The method according to claim 11, wherein each said aqueous reaction medium further contains a different antibiotic.

14. The method according to claim 11, wherein each said aqueous reaction medium further contains a different antifungal agent.

15. The method according to claim 1, wherein said at least one reaction medium is provided in a container.

16. The method according to claim 15, wherein said container is a miniaturized cup.

17. The method according to claim 15, wherein said container is a vial.

18. The method according to claim 15, wherein said container is a microtitration plate.

19. The method according to claim 1, wherein the sample is a microbial suspension prepared from a culture on a solid medium.

20. The method according to claim 1, wherein the sample is a microbial suspension prepared from a culture on a liquid medium.

21. A kit for performing the method according to claim 1, comprising at least one container, each said container containing a reagent comprising said aqueous-phase reaction medium, at least one carbon source and said marker, said marker emitting light by fluorescence directly without hydrolytic splitting and corresponding to a member selected from the group consisting of the following formula and its anionic form:

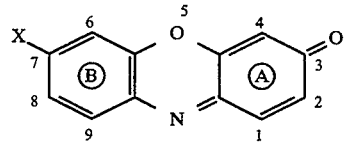

in which:
        positions (4), (6), (8) and (9) are each occupied by one of a hydrogen atom and a substituent selected from the group consisting of fluorine, chlorine, bromine and alkyl, alkoxy, carboxylate, carboxyl, amide and cyano substituents;

positions (1) and (2) are each occupied by one of a hydrogen atom and a substituent selected from the group consisting of fluorine, chlorine, bromine, and alkyl, alkoxy, carboxylate, carboxyl, amide and cyano substituents, or positions (1) and (2) belong in common to the ring (A) and to an unsaturated ring; and X is one of a hydroxyl and amine function.

22. The kit according to claim 21, comprising bottles or vials containing said reagent.

23. The method according to claim 1, wherein the fluorescence of the marker is observed during said incubating step.

24. The method according to claim 1, wherein the fluorescence of the marker is observed after said incubating step.

25. The method according to claim 1, wherein said reaction medium is contained in a bottle or vial.

26. A kit for the detection of microbes, bacteria and yeasts, comprising at least one container, each said container containing a reagent comprising an aqueous-phase reaction medium, at least one carbon source and a marker, said marker emitting light by fluorescence directly without hydrolytic splitting and corresponding to a member selected from the group consisting of the following formula and its anionic form:

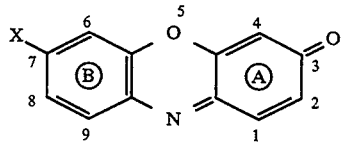

in which:

positions (4), (6), (8) and (9) are each occupied by one of a hydrogen atom and a substituent selected from the group consisting of fluorine, chlorine, bromine and alkyl, alkoxy, carboxylate, carboxyl, amide and cyano substituents;

positions (1) and (2) are each occupied by one of a hydrogen atom and a substituent selected from the group consisting of fluorine, chlorine, bromine and alkyl, alkoxy, carboxylate, carboxyl, amide and cyano substituents, or positions (1) and (2) belong in common to the ring (A) and to an unsaturated ring; and X is one of a hydroxyl and amine function.

27. The kit according to claim 26, wherein each said container further comprises at least one antibiotic.

28. The kit according to claim 26, wherein each said container further comprises at least one antifungal agent.

29. The kit according to claim 26, comprising bottles or vials containing said reagent.

* * * * *